US00PP36808P2

(12) United States Plant Patent
Roberts et al.

(10) Patent No.: US PP36,808 P2
(45) Date of Patent: Jul. 8, 2025

(54) ***HYDRANGEA* PLANT NAMED 'Bailmacnine'**

(50) Latin Name: *Hydrangea macrophylla*
Varietal Denomination: Bailmacnine

(71) Applicant: Bailey Nurseries, Saint Paul, MN (US)

(72) Inventors: David Jonathan Roberts, Athens, GA (US); Oren McBee, Bishop, GA (US); Justin Schulze, Athens, GA (US); Rebecca Orazi, Athens, GA (US)

(73) Assignee: BAILEY NURSERIES INC., Newport, MN (US)

( * ) Notice: Subject to any disclaimer, the term of this patent is extended or adjusted under 35 U.S.C. 154(b) by 0 days.

(21) Appl. No.: 19/033,437

(22) Filed: Jan. 21, 2025

(51) Int. Cl.
*A01H 6/48* (2018.01)
*A01H 5/02* (2018.01)

(52) U.S. Cl.
USPC ..... Plt./250

(58) Field of Classification Search
USPC ..... Plt./250
CPC ..... A01H 6/48; A01H 5/02
See application file for complete search history.

*Primary Examiner* — Keith O. Robinson
(74) *Attorney, Agent, or Firm* — Penny J. Aguirre

(57) ABSTRACT

A new cultivar of *Hydrangea macrophylla* plant named 'Bailmacnine' that is characterized by its compact plant habit, its cold hardiness in USDA Zone 4, its early flowering, its strong remontant blooming habit with fast re-blooming on new growth, and its inflorescences that are classic pink or blue depending on growing conditions.

3 Drawing Sheets

Botanical classification: *Hydrangea macrophylla.*
Varietal denomination: 'Bailmacnine'.

BACKGROUND OF THE INVENTION

The present invention relates to a new and distinct cultivar of *Hydrangea macrophylla* and will be referred to hereafter by its cultivar name, 'Bailmacnine'. 'Bailmacnine' represents a new mophead type *Hydrangea*, a deciduous shrub grown for use as a landscape plant.

'Bailmacnine' was derived from an ongoing breeding program conducted by the Inventors in Winterville, Georgia. The goal of the breeding program is to develop new cultivars of *Hydrangea macrophylla* with compact plant habits, faster re-blooming habits with classic blue or pink mophead inflorescences, and improved disease resistance.

The Inventors made a cross in summer 2016 between unnamed and unpatented proprietary plants in the Inventor's breeding program, reference no. HM16-06-04, as the female parent and reference no. HM16-G1-03 as the male parent. The Inventors selected 'Bailmacnine' in summer of 2017 as a single unique plant amongst the seedlings that resulted from the above cross.

Asexual propagation of the new cultivar was first accomplished by softwood stem cuttings by one of the Inventors in Winterville, Georgia in summer of 2018. Asexual propagation by softwood stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Bailmacnine' as a unique cultivar of *Hydrangea.*

1. 'Bailmacnine' exhibits a compact plant habit.
2. 'Bailmacnine' exhibits cold hardiness in USDA Zone 4.

3. 'Bailmacnine' exhibits early flowering.
4. 'Bailmacnine' exhibits a strong remontant blooming habit with fast re-blooming on new growth.
5. 'Bailmacnine' exhibits inflorescences that are classic pink or blue depending on growing conditions.

The female parent of 'Bailmacnine' differs from 'Bailmacnine' in having a less compact habit, a slower time to bloom and rebloom on new growth, and inflorescence that are darker blue or darker pink in color. The male parent of 'Bailmacnine' differs from 'Bailmacnine' in having a less compact habit, a slower time to bloom and rebloom on new growth, and larger sized inflorescences. 'Bailmacnine' can be most closely compared to the *Hydrangea macrophylla* cultivars 'Bailmer' (U.S. Plant Pat. No. 15,298) and 'SMNHSME' (U.S. Plant Pat. No. 34,327). 'Bailmer' is similar to 'Bailmacnine' in having classic blue or pink lace-cap type flowers and a remontant blooming habit. 'Bailmer' differs from 'Bailmacnine' in having a more compact plant habit, darker green foliage, more blooms, and a faster time to rebloom, and in being easier to turn blooms blue under bluing conditions. 'SMNHSME' is similar to 'Bailmacnine' in having a compact plant habit, blue or pink inflorescences, and a remontant blooming habit. 'SMNHSME' differs from 'Bailmacnine' in having darker green foliage and in being slower to rebloom.

BRIEF DESCRIPTION OF THE DRAWINGS

The accompanying color photographs illustrate the overall appearance and distinct characteristics of the new *Hydrangea*. The photograph was taken of 2-year-old plants of 'Bailmacnine' as grown in 2-gallon containers in a greenhouse in Cottage Grove, Minnesota.

The photograph in FIG. 1 provides a side view of 'Bailmacnine' in bloom.

Figure 1:
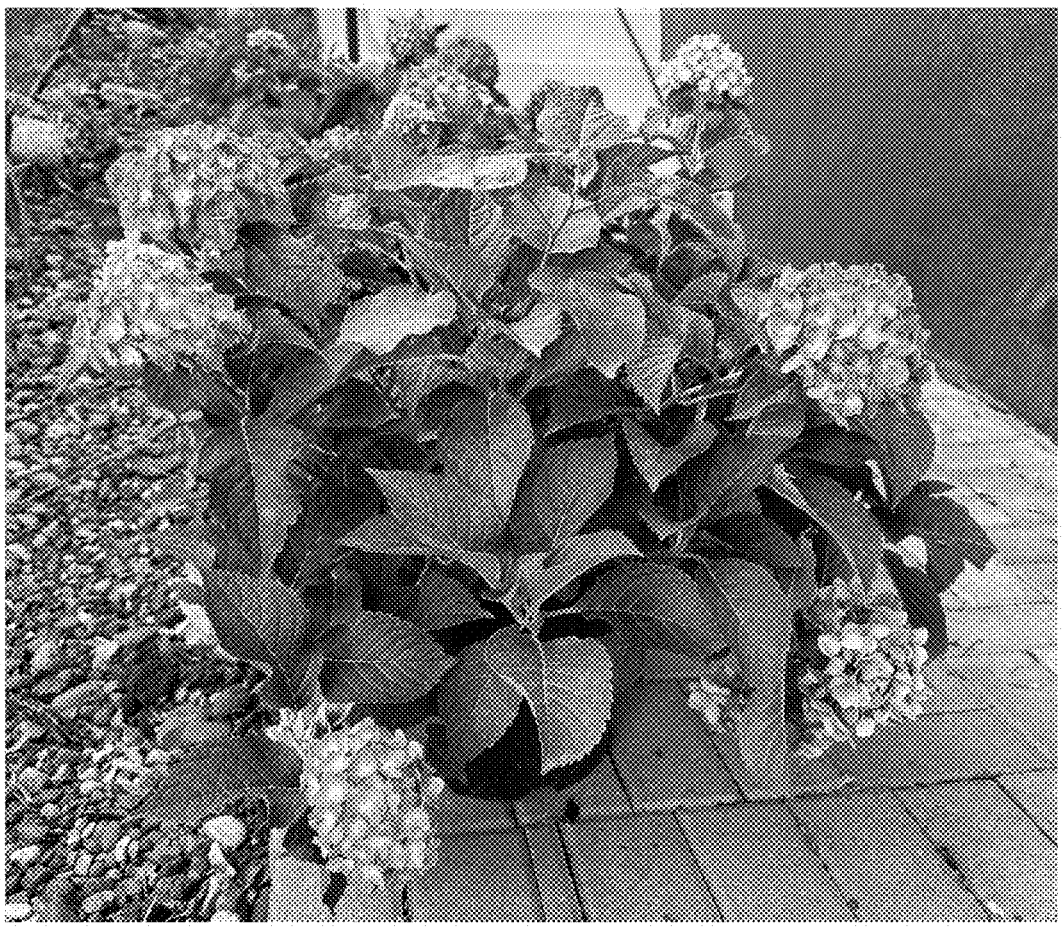
Figure 2:
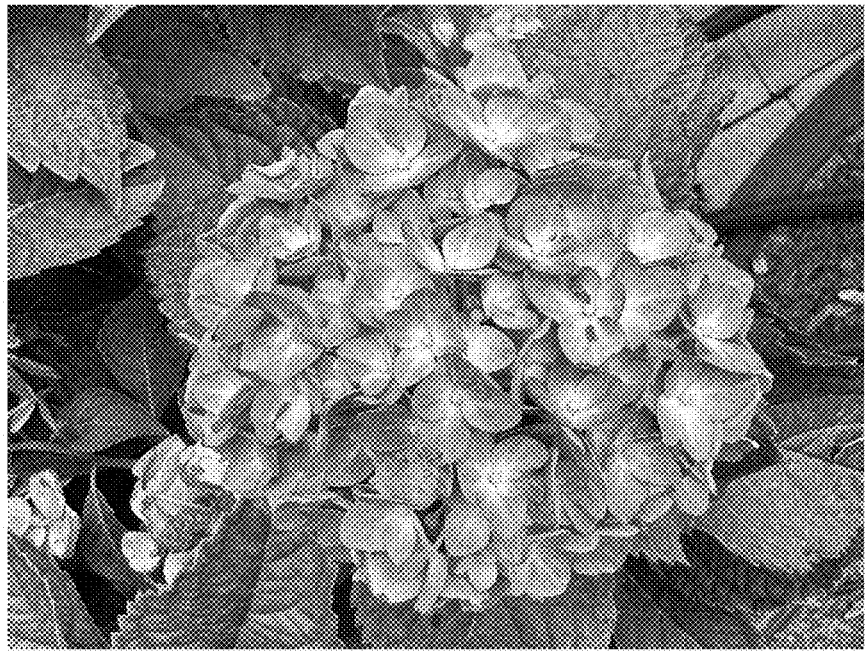

The photograph in FIG. 2 provides a close-up view of an inflorescence of 'Bailmacnine' when grown under non-bluing conditions.

Figure 3:
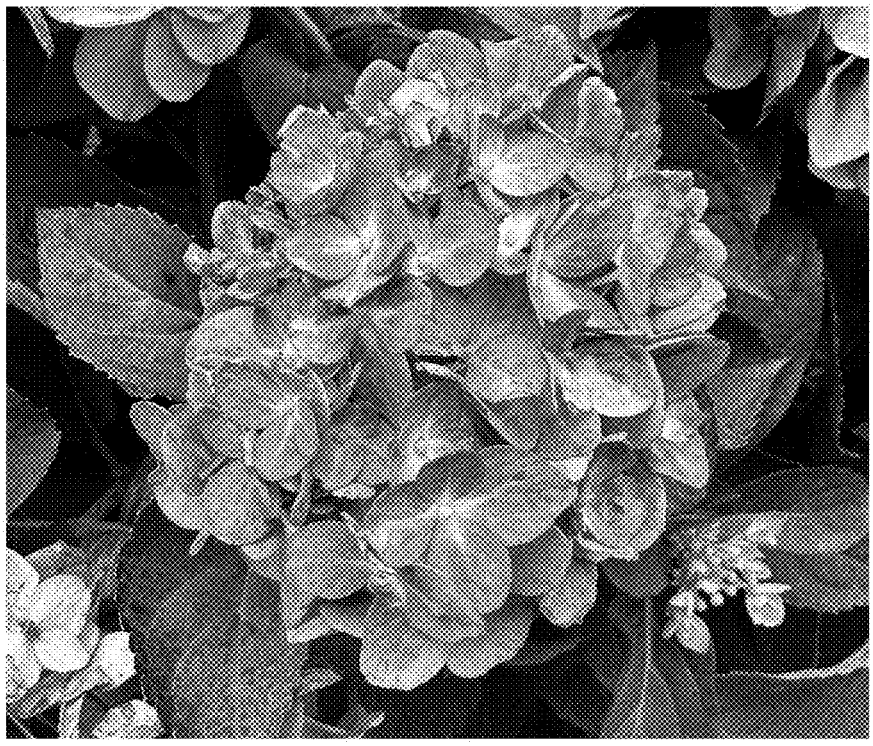

The photograph in FIG. 3 provides a close-up view of an inflorescence of 'Bailmacnine' grown under bluing conditions.

Figure 4:
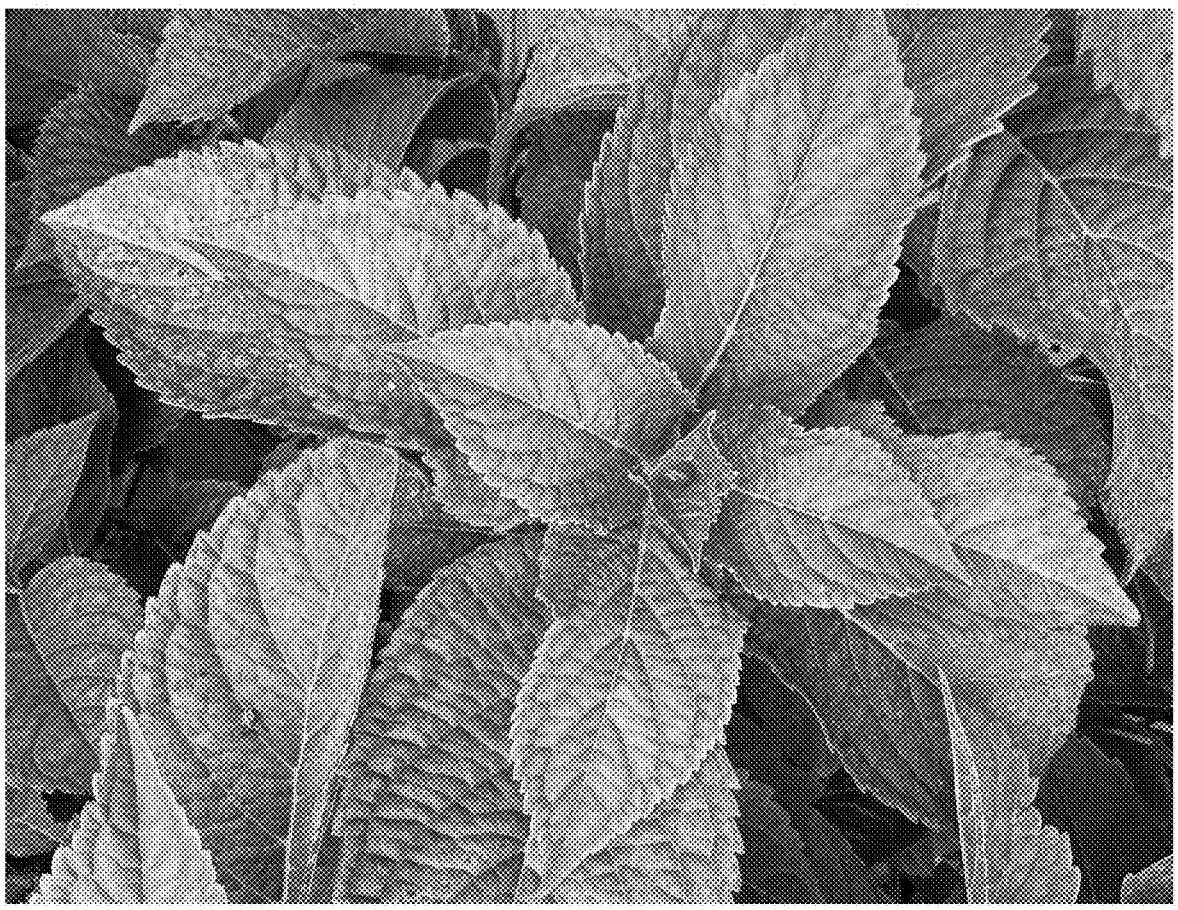

The photograph in FIG. 4 provides a close-up view of the foliage of 'Bailmacnine'.

The colors in the photographs are as close as possible with the photographic and printing technology utilized and the color values cited in the detailed botanical description accurately describe the colors of the new *Hydrangea.*

BOTANICAL DESCRIPTION OF THE PLANT

The following is a detailed description of 2-year-old plants of 'Bailmacnine' as grown in 2-gallon containers in a greenhouse in Cottage Grove, Minnesota. The data was primarily taken on plants that were grown in alkaline soils with some additional data provided when plants were grown in acidic soil with sufficient aluminum sulfate (bluing conditions). The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period.*—Late May to frost in Winterville, GA.

*Plant type.*—Deciduous shrub, mophead type *Hydrangea.*

*Plant habit.*—Compact, mounded.

*Height and spread.*—Average of 54 cm in height and 83 cm in spread as grown in a 2-gallon container, reaches 91 cm in height and width as grown in the landscape in Georgia.

*Hardiness.*—At least to USDA Zones 4 to 9.

*Diseases.*—No resistance or susceptibility to diseases has been observed.

*Root description.*—Fine and fibrous, 199B in color.

*Propagation.*—Softwood stem cuttings.

*Growth rate.*—Moderate.

*Root development.*—Time required for root initiation is 20 days, time required to produce a young plant from a rooted cutting is 60 days.

Stem description:

*Stem shape.*—Rounded.

*Stem strength.*—Strong.

*Stem color.*—Young; 145A to 145B, mature; 144B, flushed with 183A, old growth at base; a blend of 199B and 200B.

*Stem size.*—Main branches; average of 15 cm in length, 1 cm in diameter, lateral branches; average of 20 cm in length, 5 mm in diameter.

*Stem surface.*—Younger and mature stems; glabrous, sparsely to moderately lenticellate, lenticles; 10 per cm2, an average of 0.8 mm in length and 0.5 mm in width, 183A in color, old growth at base; bark-like, rugose, slightly peeling. Internode length.—Average of 4.5 cm.

*Branching.*—Average of 8 main branches, average of 4 to 8 lateral branches per main branch.

*Stipules.*—Persistent, 2 opposite at base of petioles, stipule bud; is 5 mm in length, 1 mm in width, 183A in color, oblong in shape, acute apex, glossy and glabrous surface, stipule leaves; 1 cm in length, 4 mm in width, acute apex, serrate to entire margins, each leaf fused into base, opposite, both surfaces glossy, both surfaces 137A, base and veins 144B in color.

Foliage description:

*Leaf shape.*—Ovate to broadly ovate.

*Leaf arrangement.*—Opposite.

*Leaf division.*—Simple.

*Leaf base.*—Attenuate.

*Leaf apex.*—Acute to bluntly acute.

*Leaf margins.*—Serrate.

*Leaf venation.*—Pinnate, upper surface; 145C, lower surface; 145A and 145C in color.

*Leaf size.*—Matures to an average of 15 cm in length and 9 cm in width.

*Leaf attachment.*—Petiolate.

*Leaf surface.*—Upper surface; matte, rugose with veins impressed, very sparsely covered with stiff short hairs, NN155D in color, 0.4 mm in length, lower surface; glabrous, matte with a slight argenteous sheen.

*Leaf color.*—Young upper and lower surface; 145A, mature upper surface 147B, lower surface 147B, slight argenteous sheen 191A.

*Petioles.*—An average of 2.5 cm in length and 3 mm in diameter, both surfaces 145C in color, glabrous, and matte.

Inflorescence description:

*Inflorescence type.*—Terminal panicle, mophead in form, comprised of fertile flowers and single sterile flowers.

*Lastingness of inflorescence.*—Persistent for 3 months.

*Inflorescence number.*—One per lateral stem.

*Inflorescence size.*—Average of 9 cm in height, 12 cm in diameter.

*Flower number.*—Average of 80 sterile flowers and 200 fertile flowers per panicle.

*Flower fragrance.*—None.

*Flower aspect.*—Upright to outward.

*Flower size.*—Sterile flowers; an average of 4 cm in diameter and 5 mm in depth, fertile flowers; an average of 5 mm in diameter and 2 mm in depth.

*Flower type.*—Rotate.

*Flower buds.*—Sterile flowers; average of 2 mm in length and diameter, obovate in shape, color is 144A to 144B, fertile flowers; average of 3 mm in width and 2 mm in diameter, broad obovate in shape, color; 150D with flushes of 150C and 68A, for plants grown under bluing conditions 98C and 98A.

*Peduncles.*—Strong, average of 1 cm in length and 2 mm in width, surface is slightly shiny and sparsely covered with very fine pubescence and lenticels.

*Pedicels.*—Sterile flowers; strong, average of 2 cm in length and 1 mm in width, surface is slightly shiny and moderately covered with very fine woolly hairs that match surface color, color; 66A, color under bluing conditions; 96A to 96B, fertile flowers; strong, average of 3 mm in length and 1 mm in width, surface is slightly shiny and moderately covered with very fine woolly hairs that match surface color to NN155A in color, color; 66A, color under bluing conditions; 96A to 96B.

*Petals.*—Sterile flowers: petal spot (flower bud); round in shape, average of 1 mm in length and diameter, young bud 145A, changing to 155A, before burst 75A to 75B, after burst; average of 5 petals, 2 mm in length, 1.2 mm in width, both surfaces are satiny and dull, acute apex, rotate arrangement, cuneate base, entire margins, ovate and concave in shape, color: when opening and fully open upper and lower surface; 72B and 72C, dropping after maturity, for plants grown under bluing conditions; color: young bud 145A, before burst a blend of 101D, 100A to 100B, after burst; when opening and fully open upper and lower surface; 104A, dropping after maturity, fertile flowers: flower bud; obovate in shape, average of 1 mm in depth and diameter, before burst 145A in color, after burst; average of 5 petals, both surfaces are satiny and dull, acute apex, rotate arrangement, cuneate base, entire margins, concave in shape, color: when opening and lower surface; 73A to 73B, when fully open upper and lower surface; 68A, becoming 72A before dropping, for plants grown under bluing conditions; young buds N144A in color, before burst 101C to 101D in color, after burst; 101C to 101D, when opening and fully open upper and lower surfaces 101A to 101B, fading; petals drop after maturity.

*Sepals*.—Sterile flowers (showy); 4 to 5, broad rhomboidal in shape, slightly overlapping, rotate in arrangement, entire margin, apex is very slightly retuse to bluntly pointed, cuneate base, average of 2 cm in length and 1.5 cm in width, upper and lower surface glabrous and satiny, color: before bud burst 145A, after bud burst upper and lower surface; 155B, becoming flushed with 68D, when opening upper and lower surface; 68D, fully open upper and lower surface; a blend of 65A, 68A, and 69D, mature and fading; a blend of 196A and 145B, for plants grown under bluing conditions: when opening; 149C, flushed on the edges with 101C, when fully open upper and lower surface; a blend of 98A, 98D, flushed with N74B, mature and fading upper and lower surface; a blend of 145A, 100A and 100B, eventually becoming a blend of 164A to 164B, fertile flowers; 5, rotate in arrangement, ovate in shape, entire margin, acute apex, cuneate base, average of 0.5 mm in length and width, both surfaces are glabrous, color: young upper and lower surface; 145A, mature upper and lower surface; 145D, for plants grown under bluing conditions; young upper and lower surface; N144A, mature upper and lower surface; 145B.

Reproductive organs:

*Stamens*.—Sterile flowers; emerging from petal spot; 4 to 5, anther; broadly reniform in shape, 1 mm in length and width, 72A and 200A in color, under bluing conditions 99A in color, filament; 3 mm in length, 0.3 mm in width and 72A in color, under bluing conditions 99A in color, pollen is moderate in quantity and NN155D in color, fertile flowers; average of 5, anther is broad reniform in shape, 0.5 mm in length and 72A in color, under bluing conditions 99A in color, filament is 5 mm in length and 72A in color, under bluing conditions 99A in color, pollen is moderate in quantity and NN155D in color.

*Pistils*.—Sterile flowers; emerging from petal spot; 3 to 4, average of 1 mm in length, 0.5 mm in width, stigma is round in shape and 77A in color, under bluing conditions 99A in color, 0.5 mm in length and diameter, style is an average of 1.5 mm in length and 77A in color, under bluing conditions 99A in color, ovary is 77A in color, under bluing conditions 99A in color, fertile flowers; average of 4, an average of 2 mm in length, stigma is clavate in shape and 77A in color, under bluing conditions 99A in color, style is 77A in color, under bluing conditions 99A in color, ovary is 99A in color.

*Fruit and seed*.—Not observed to date.

It is claimed:

1. A new and distinct cultivar of *Hydrangea* plant named 'Bailmacnine' substantially as herein illustrated and described.

* * * * *